United States Patent
He et al.

(10) Patent No.: US 9,132,209 B2
(45) Date of Patent: Sep. 15, 2015

(54) SURFACE CROSSLINKED POLYETHYLENE

(75) Inventors: Shulin He, Montvale, NJ (US); Zongtao Zhang, Riverdale, NJ (US); Keenan Michael Hanson, Tuxedo, NY (US); Shi-Shen Yau, Berkeley Heights, NJ (US)

(73) Assignee: Howmedia Osteonics Corp., Mahwah, NJ (US)

( * ) Notice: Subject to any disclaimer, the term of this patent is extended or adjusted under 35 U.S.C. 154(b) by 567 days.

(21) Appl. No.: 12/775,789

(22) Filed: May 7, 2010

(65) Prior Publication Data

US 2011/0276143 A1    Nov. 10, 2011

(51) Int. Cl.
*A61L 27/50* (2006.01)
*A61L 27/16* (2006.01)

(52) U.S. Cl.
CPC .............. *A61L 27/50* (2013.01); *A61L 27/16* (2013.01); *A61L 2400/18* (2013.01); *A61L 2430/02* (2013.01)

(58) Field of Classification Search
CPC ............ C08L 23/06; A61F 2/30; A61F 2/34; A61F 2/38; C08F 2/48; C08F 2/50; C08F 4/6094; A61L 27/50; A61L 27/16; A61L 2400/18; A61L 2403/02
USPC ....................... 522/161, 46; 623/18.11, 23.58; 427/2.24, 2.26
See application file for complete search history.

(56) References Cited

U.S. PATENT DOCUMENTS

| | | |
|---|---|---|
| 5,073,611 A | 12/1991 | Rehmer et al. |
| 5,225,495 A * | 7/1993 | Han et al. ............. 525/327.4 |
| 5,505,900 A | 4/1996 | Suwanda et al. |
| 5,567,435 A | 10/1996 | Hubbell et al. |
| 6,165,220 A | 12/2000 | McKellop et al. |
| 6,281,264 B1 | 8/2001 | Salovey et al. |
| 6,494,917 B1 | 12/2002 | McKellop et al. |
| 6,677,030 B2 | 1/2004 | Thakkar et al. |
| 6,709,742 B2 | 3/2004 | Ladika et al. |
| 6,800,670 B2 | 10/2004 | Shen et al. |

(Continued)

FOREIGN PATENT DOCUMENTS

| | | |
|---|---|---|
| EP | 0490854 A2 | 6/1992 |
| EP | 1433488 A1 | 6/2004 |

(Continued)

OTHER PUBLICATIONS

Chen et al., Journal of Polymer Science, Part A, Polymer Chemistry, vol. 27, No. 12, pp. 4051-4075, 1989.
Chen et al., Journal of Polymer Science, Part A, Polymer Chemistry, vol. 27, pp. 4077-4086, 1989.
Chen et al., Polymers for Advanced Technologies, vol. 1, pp. 103-107.

(Continued)

*Primary Examiner* — Mark Eashoo
*Assistant Examiner* — Jessica Roswell
(74) *Attorney, Agent, or Firm* — Lerner, David, Littenberg, Krumholz & Mentlik, LLP

(57) ABSTRACT

A method for producing a wear resistant polyethylene medical implant includes forming a medical implant, such as an orthopedic implant, made at least partially of ultra high molecular weight polyethylene (UHMWPE). The polyethylene may be irradiated with gamma ray or e-beam radiation to form free radicals and then crosslinked to eliminate free radicals prior to exposure to oxygen. The so treated bearing surface of the crosslinked polyethylene is then coated with a photoinitiator. Thereafter the bearing material is photo-crosslinked with ultra-violet (UV) radiation. The photo-crosslinking process can also be applied to non-crosslink UHMWPE.

25 Claims, 4 Drawing Sheets

(56) References Cited

U.S. PATENT DOCUMENTS

| | | |
|---|---|---|
| 7,282,165 B2 | 10/2007 | Williams, III et al. |
| 7,384,430 B2 | 6/2008 | Greer et al. |
| 7,517,919 B2 | 4/2009 | Wang et al. |
| 7,635,725 B2 | 12/2009 | Bellare et al. |
| 2004/0243249 A1 | 12/2004 | Ishihara et al. |
| 2007/0270970 A1 | 11/2007 | Trieu |
| 2007/0270971 A1 | 11/2007 | Trieu et al. |
| 2009/0105439 A1 | 4/2009 | Wang et al. |
| 2009/0306781 A1 * | 12/2009 | Kyomoto et al. .......... 623/18.11 |

FOREIGN PATENT DOCUMENTS

| | | | |
|---|---|---|---|
| EP | 1987849 A1 | 11/2008 | |
| EP | 2002854 A2 | 12/2008 | |
| JP | 2007536998 A | 12/2007 | |
| WO | 9521212 A1 | 8/1995 | |
| WO | 2005110276 A1 | 11/2005 | |
| WO | WO 2007/091521 * | 8/2007 | .............. A61L 27/00 |
| WO | 2010023447 A1 | 3/2010 | |

OTHER PUBLICATIONS

Herrera et al., Wear, 263, pp. 1034-1037, 2007.
Liu et al., Polymer Degradation and stability, 49: 151-161, 1995.
Muratoglu et al., Biomaterials, 20: 1463-1470, 1999.
Oral et al., Highly Improved Mechanical Properties of Surface Crosslinked UHMWPE, 56th Annual Meeting of the Orthopaedic Research Society, Mar. 18, 2010.
Salem, MA. Egypt J. Sol., vol. 24, No. 2, pp. 141-150, 2001.
Wu et al., Polymer Engineering and Science, vol. 41, No. 7, Jul. 2001.
Zamotaev et al., Applied Macromolecular Chemistry and Physics, 210, pp. 119-128, 1993.
European Search Report, EP 11164668, dated Oct. 19, 2011.
Tincer T et al: "Drawing behaviour of high density polyethylene crosslinked by ultraviolet radiation in the presence of acetophenone", International Journal of Radiation Applications and Instrumentation. Part C. Radiation Physics and Chemistry, Pergamon, vol. 36, No. 3, Jan. 1, 1990, pp. 345-351, XP024483140.
Japanese Office Action for Application No. 2011-103628 dated Feb. 17, 2015.

* cited by examiner

SURFACE CROSSLINKED POLYETHYLENE

BACKGROUND OF THE INVENTION

Ultra High molecular weight polyethylene (UHMWPE) has been used as a bearing material for artificial joints such as hips and knees. Highly crosslinked UHMWPE is the current state-of-the-art for orthopedic bearing applications. Gamma or e-beam irradiation is the standard process to crosslink UHMWPE with practical irradiation dose about 3-10 Mrads. In this dose range, the wear rate is about 2.5 mm3/Mc at 9.5 Mrads and 20 mm3/Mc at 3.3 Mrads, respectively (See FIG. 22, U.S. Pat. No. 6,800,670 B2). Continuing increase of irradiation dose from 10 to 50 Mrads gradually drops the wear rate towards zero, but the material becomes too brittle for clinical use. It is desirable for UHMWPE that have wear rate about zero without increasing irradiation dose above 10 Mrads, thus mechanical properties does not suffer.

This invention relates to medical implants formed of a polymeric material such as ultra-high molecular weight polyethylene, with superior oxidation and wear resistance produced by an irradiation and annealing process followed by UV surface crosslinking. Alternatively the UHMWPE base material could be virgin UHMWPE or doped with an antioxidant such as anthocyanin.

Various polymer systems have been used for the preparation of artificial prostheses for biomedical use, particularly orthopedic applications. Among them, ultra-high molecular weight polyethylene is widely used for articulation surfaces in artificial knee, hip, and other joint replacements. Ultra-high molecular weight polyethylene (UHMWPE) has been defined as those linear polyethylenes which have a relative viscosity of 2.3 or greater at a solution concentration of 0.05% at 135° C. in decahydronaphthalene. The nominal weight–average molecular weight is at least 400,000 and up to 10,000,000 and usually from three to six million. The manufacturing process begins with the polymer being supplied as fine powder which is consolidated into various forms, such as rods and slabs, using ram extrusion or compression molding. Afterwards, the consolidated rods or slabs are machined into the final shape of the orthopedic implant components. Alternatively, the component can be produced by compression molding of the UHMWPE resin powder.

It has been recognized that regardless of the radiation type, the high energy beam causes generation of free radicals in polymers during radiation. It has also been recognized that the amount or number of free radicals generated is dependent upon the radiation dose received by the polymers and that the distribution of free radicals in the polymeric implant depends upon the geometry of the component, the type of polymer, the dose rate, and the type of radiation beam. The generation of free radicals can be described by the following reaction (which uses polyolefin and gamma ray irradiation for illustration):

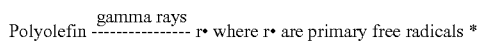

(1)

\* (through C—C chain scission or C—H scission)

If oxygen is present, primary free radicals r. will react with oxygen and the polymer according to the following reactions as described in "Radiation Effects on Polymers," edited by Roger L. Clough and Shalaby W. Shalaby, published by American Chemical Society, Washington, D.C., 1991.

In the Presence of Oxygen

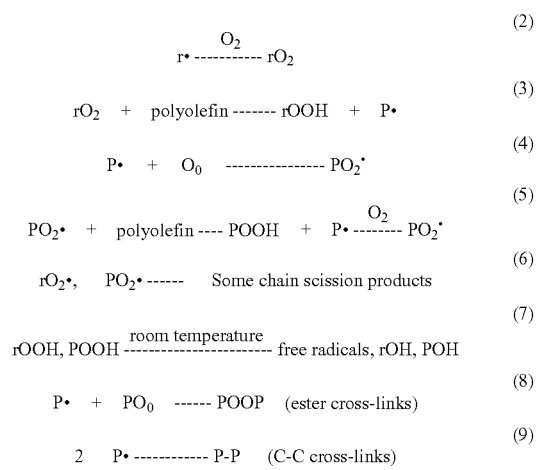

In radiation in air, primary free radicals r. will react with oxygen to form peroxyl free radicals $rO_2\cdot$, which then react with polyolefin (such as UHMWPE) to start the oxidative chain scission reactions (reactions 2 through 6). Through these reactions, material properties of the plastic, such as molecular weight, tensile and wear properties, are degraded.

It has been found that the hydroperoxides (rOOH and POOH) formed in reactions 3 and 5 will slowly break down as shown in reaction 7 to initiate post-radiation degradation. Reactions and 9 represent termination steps of free radicals to form ester or carbon-carbon cross-links. Depending on the type of polymer, the extent of reactions 8 and 9 in relation to reactions 2 through 7 may vary. For irradiated UHMWPE, a value of 0.3 for the ratio of chain scission to cross-linking has been obtained, indicating that even though cross-linking is a dominant mechanism, a significant amount of chain scission occurs in irradiated polyethylene.

By applying radiation in an inert atmosphere, since there is no oxidant present, the primary free radicals r. or secondary free radicals P. can only react with other neighboring free radicals to form carbon-carbon cross-links, according to reactions 10 through 12 below. If all the free radicals react through reactions 10 through 12, there will be no chain scission and there will be no molecular weight degradation. Furthermore, the extent of cross-linking is increased over the original polymer prior to irradiation. On the other hand, if not all the free radicals formed are combined through reactions 10, 11 and 12, then some free radicals will remain in the plastic component.

Out of Contact with Oxygen

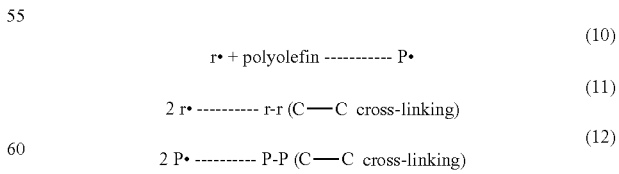

It is recognized that the fewer the free radicals, the better the polymer retains its physical properties over time. The greater the number of free radicals, the greater the degree of molecular weight and polymer property degradation will occur. Applicant has discovered that the extent of completion of free radical cross-linking reactions is dependent on the reaction rates and the time period given for reaction to occur.

UHMWPE is commonly used to make prosthetic joints such as artificial hip joints. In recent years, it has been found that tissue necrosis and interface osteolysis may occur in response to UHMWPE wear debris. For example, wear of acetabular cups of UHMWPE in artificial hip joints may introduce microscopic wear particles into the surrounding tissues.

Improving the wear resistance of the UHMWPE socket and, thereby, reducing the rate of production of wear debris may extend the useful life of artificial joints and permit them to be used successfully in younger patients. Consequently, numerous modifications in physical properties of UHMWPE have been proposed to improve its wear resistance.

It is known in the art that ultrahigh molecular weight polyethylene (UHMWPE) can be cross-linked by irradiation with high energy radiation, for example gamma or e-beam radiation, in an inert atmosphere or vacuum. Exposure of UHMWPE to gamma irradiation induces a number of free-radical reactions in the polymer. One of these is cross-linking. This cross-linking creates a 3-dimensional network in the polymer which renders it more resistant to adhesive wear in multiple directions. The free radicals formed upon irradiation of UHMWPE can also participate in oxidation which reduces the molecular weight of the polymer via chain scission, leading to degradation of physical properties, embrittlement and a significant increase in wear rate. The free radicals are very long-lived (greater than eight years), so that oxidation continues over a very long period of time resulting in an increase in the wear rate as a result of oxidation over the life of the implant.

Sun et al. U.S. Pat. No. 5,414,049, the teachings of which are incorporated herein by reference, broadly discloses the use of radiation to form free radicals and heat to form cross-links between the free radicals prior to oxidation.

Hyun et al. U.S. Pat. No. 6,168,626 relates to a process for forming oriented UHMWPE materials for use in artificial joints by irradiating with low doses of high-energy radiation in an inert gas or vacuum to cross-link the material to a low degree, heating the irradiated material to a temperature at which compressive deformation is possible, preferably to a temperature near the melting point or higher, and performing compressive deformation followed by cooling and solidifying the material. The oriented UHMWPE materials have improved wear resistance. Medical implants may be machined from the oriented materials or molded directly during the compressive deformation step. The anisotropic nature of the oriented materials may render them susceptible to deformation after machining into implants.

Salovey et al. U.S. Pat. No. 6,228,900, the teachings of which are incorporated by reference, relates to a method for enhancing the wear-resistance of polymers, including UHMWPE, by cross-linking them via irradiation in the melt.

Saum et al. U.S. Pat. No. 6,316,158 relates to a process for treating UHMWPE using irradiation followed by thermally treating the polyethylene at a temperature greater than 150° C. to recombine cross-links and eliminate free radicals.

Sequential crosslinking is described in U.S. Pat. No. 7,517,919, the disclosure of which is incorporated by reference. An UHMWPE crosslinked three times as disclosed in U.S. Pat. No. 7,517,919 is designated herein as "X3", a registered trademark of Stryker Corporation.

In the present invention ultraviolet (UV) radiation is applied to photocrosslink a UHMWPE bearing surface to generate an additional surface crosslinking layer on the already gamma or e-beam crosslinked bulk UHMWPE implant. The implant may be previously crosslinked at a dosage range between 1-10 Mrads or even higher. The surface layer thickness is controlled to a depth of about 100 micrometers. In this range, the surface layer can last at least 5 million cycles in a wear simulator test without showing measurable wear which can be seen by maintaining the original machining marks on the bearing surface.

Ultraviolet (UV) light crosslinking has been used for crosslinking polyethylene since the 1950's. In the past UV was used to crosslink polyethylene (PE) bulk material, fibers, and films by mixing a photo-initiator and PE resin, then consolidating the resin and crosslinking under UV irradiation (see for example U.S. Pat. No. 6,281,264 B1, Chen Y. L. et al., "Photocrosslinking of Polyethylene", Journal Polymer Science, Polymer Chemistry Edition, 1989, Qu B. J., et al., "Photoinitiating Characteristics Of Benzophenone Derivatives As New Initiators In The Photocrosslinking Of Polyethylene, Polymer Engineering and Science, July 2001). On the other hand, PE degradation in air when exposed in sun light (low UV intensity) is a well-known phenomena. To prevent this, PE, an anti-UV additive is sometimes added to the polyethylene resin. However, none of the prior art disclosed using UV as a surface crosslinking method for a consolidated UHMWPE bearing, nor using a UV method to generate an additional crosslinking layer on a gamma or e-beam irradiated crosslinked UHMWPE bearing material for orthopedic applications such as in acetabular cup, glenoid bearings, tibial bearing surfaces, finger and elbow UHMWPE bearings. U.S. Pat. No. 6,165,220 relates to e-beam surface crosslinking. U.S. Patent Publication No. 20070270970 relates to polymeric bearings for use in the spine.

UV crosslinking of polyethylene is a reaction of carbon center free radicals that are generated by UV radiation. Mechanism of the UV crosslinking of polyethylene is briefly described below. When UV light radiates polyethylene that contains benzophenone, a photoinitiator, benzophenone absorbs UV energy and jumps to the excited triplet state. The benzophenone in the triplet excited state abstracts hydrogen from polyethylene to generate polyethylene carbon radicals. The formed PE carbon center radicals undergo free radical reaction to form crosslinking.

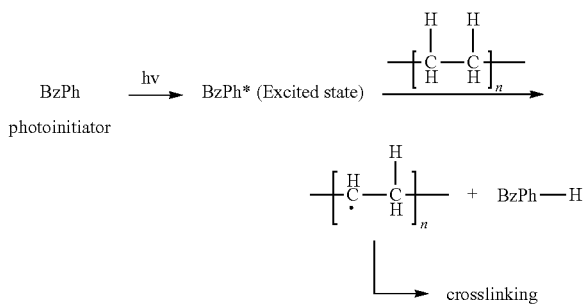

The quantum yield of the excited triplet state is very high for benzophenone and the triplet state is highly effective in hydrogen extraction. It is noted that there is no carbon-carbon bond breakage in the UV crosslinking process and the carbon radicals are generated solely by a carbon-hydrogen bond cleavage. Therefore, unlike gamma or e-beam crosslinking process, UV crosslinking does not result in a reduction of molecular weight.

Due to improved surface wear performance of surface photocrosslinked already bulk crosslinked UHMWPE, acetabular UHMWPE cups can be designed to be very thin (<3 mm)

without the danger of wearing through. The current FDA standard is 6.0 mm thick UHMWPE. A thinner cup will maximize femoral head size. The bigger femoral head size can significantly decrease rate of dislocation, which is the number one cause of total hip replacement revision. Another benefit of the very thin UHMWPE bearing is to allow cobalt-chrome-on-UHMWPE for resurfacing hip applications. Current resurfacing bearing are typically cobalt chrome on cobalt chrome which may release metal ions which causes metal hypersensitivity in some patients.

Another benefit of the present invention is for knee tibial insert applications. One of the causes of knee revision is that the tibial implant is set on a soft bone bed. Overtime after implantation, the soft tibia bone allows the implant to sink to a lower position and the gap between femoral and tibia is increased, resulting in higher impact force accelerated wear of tibia insert. This invention allows the tibia insert becomes thinner, such as 3 mm, as compared to the normal 6 mm standard. The thinner tibia insert requires less of a bone cut. The bone in both femoral and tibia sides has a hardness gradient. The closer to the bearing portion of the knee joint, the harder the bone. Thus the thinner bone cut allows the knee implants to be set on the stronger bone.

Typically wear rates are higher than 2.5 mm/million cycles for 10 Mrads gamma irradiated bulk UHMWPE.

Thus additional UV surface photo-crosslinking performed on gamma ray or e-beam already crosslinked material unexpectedly produces lower wear than current crosslinked UHMWPE. The final wear performance is significantly improved as compared to the non-UV surface crosslinked surface made of highly crosslinked UHMWPE. The improved photocrosslink surface allows the use of alternate bearing material such as PAEK in general and PEEK in particular.

BRIEF SUMMARY OF THE INVENTION

UV cross-linking is a non-ionized crosslinking method. During the crosslinking process, only C—H bonds in UHMWPE are cleavaged and then cross-linked. Therefore, there is no C—C bond breaking and no molecular weight decrease possible after crosslinking.

UV only crosslinks a surface layer to improve wear resistance, while the whole bulk materials can be kept in virgin condition or low cross-linked condition (such as the N2-Vac process). N2-Vac is treating the UHMWPE with 3 Mrad in less than 1% oxygen (nitrogen) without subsequent annealing. Therefore, the whole component has high fracture toughness (FIG. 4). This is especially beneficial for tibial inserts, the UV cross-linked layer thickness could be <200 micron which is much less than 1-2 mm, the depth of von Mises stress under bearing surface. Therefore, the UV cross-linked bearing has low adhesion surface wear and less fatigue wear (pitting and delamination).

A method for producing a wear resistant polyethylene medical implant, such as an orthopedic implant, comprises forming a medical implant, at least partially from ultra high molecular weight polyethylene (UHMWPE). The UHMWPE may be irradiated with gamma ray or e-beam radiation to form free radicals followed by crosslinking the formed free radicals using heat prior to exposure to air. Alternatively, the UHMWPE may be infused with an antioxidant (vitamin E, anthocyanin as discussed in U.S. Patent Publication No. 20100036491, the disclosure of which is incorporated herein by reference). The bearing surface of the crosslinked polyethylene is coated with a photoinitiator. After the coating has dried the coated surface is crosslinked with ultra-violet (UV) radiation. Preferably the photoinitiator is Benzophenone. The coating with the Benzophenone may be performed by vapor deposition. Alternately the coating with Benzophenone may be done by immersion in an acetone solution of Benzophenone at a preferred concentration of 1-100 mg Benzophenone/ml of acetone and more preferably being 10 mg/ml. If crosslinked prior to UV photocrosslinking the irradiation with gamma ray or e-beam radiation and crosslinking may be performed sequentially as described in U.S. Pat. No. 7,517,919. Each radiation dose using this method is less than or equal to 3.0 MRads. The coating process is such that the photoinitiator can penetrate the UHMWPE to a depth of between 200 microns and 1 mm. The depth depends on soak time in the photoinitiator. The implant is allowed to cool between gamma ray or e-beam crosslinking and the photocrosslinking. The photocrosslinking preferably occurs about 65° C. or between 65° C. and room temperature.

Photoinitiators which could be used include 2-methylanthraquinone, 2-ethylanthraquinone, 2-chloroanthraquinone, p-chloranil, benzyl sulfide, benzyl sulfoxide, phenyl sulfoxide, 4-acetylbiphenyl, anthrone, hexachlorobenzene, benzophenone, 4,4'-dimethoxybezophenone, 4-Nitrobenzophenone, 2-chlorobenzophenone, 4-chlorobenzophenone and 4,4'-dichlorobenzophenone.

The UV light used in the photocrosslinking preferably has a wavelength of 300 to 400 nm, and most preferably 350 nm. The intensity of the light can be up to 100 mW/cm$^2$ but preferably 50 mW/cm$^2$.

The UV cross-linking can be done in an oxygen-free medium. The oxygen-free reaction medium includes oxygen-free water and insert atmosphere. The reaction temperature can be up to the melting temperature of UHMWPE (about 135° C.).

The UV cross-linking method allows selectively crosslinks only the bearing surface, while non-bearing surfaces may be masked and are not further surface crosslinked. This maximizes wear resistance capability and avoids any property degradation which may lead to breaking the component (such as a polyethylene post of a tibial insert).

UV cross-linking is a low cost process, as compared to gamma and e-beam processes.

DETAILED DESCRIPTION

Example 1

Commercially available polyethylene acetabular cups (N2Vac according to the process of Stryker U.S. Pat. No. 5,414,049), or Virgin GUR 1020 UHMWPE which was sequentially crosslinked three times per Stryker U.S. Pat. No. 7,517,919 and obtained from Stryker orthopaedics) were used. The UV light with a wavelength of 350 nm was used as a light source. Benzophenone from Aldrich was used as a photoinitiator.

The UV crosslinking process is described below. Several already bulk crosslinked UHMWPE acetabular cups were immersed in an acetone solution of benzophenone. After one minute, each cup was taken out from the solution and dried under vacuum for an hour. The cups were immersed in deionized water in a glass jar that was purged with an inert gas (nitrogen) to produced oxygen free water. The glass jar was sealed and placed in a water bath at 65° C. Each cup was then irradiated by the UV light for up to 2 hours. After photoirradiation (which produces photocrosslinking (PXL)), each cup was washed with acetone and water. No visual changes were observed during this process. The photocrosslinked (PXL) cups were tested in a hip stimulator machine for its wear performance. Cobalt chrome and plastic ball heads (PEEK) were used against one of the UV crosslinked cups. Untreated cups were used as control. Wear testing was conducted in house following the ASTM standard method. Gravimetric wear was obtained using ASTM F2025. The soak time was 1 minute in 10 mg benzophenone per ml of acetone. The UV radiation was 50 milliwatts per $cm^2$ and wavelength of 350 nm (average).

Figure 1:
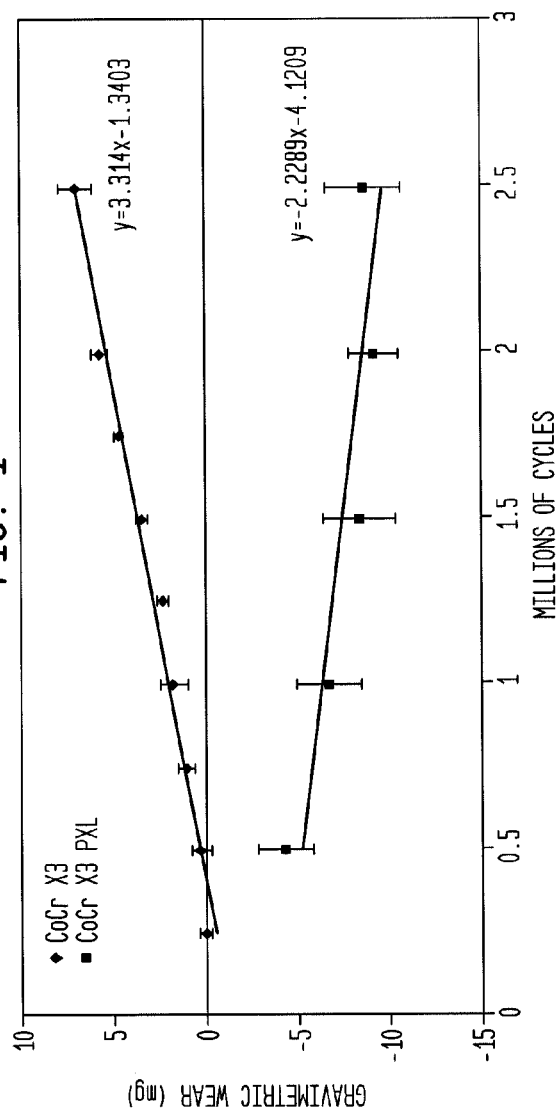
FIG. 1 is a graph showing the gravimetric wear of cobalt chrome on a sequentially crosslinked polyethylene (x3) and the same sequentially crosslinked polyethylene including photocrosslinking (PXL)
Figure 2:
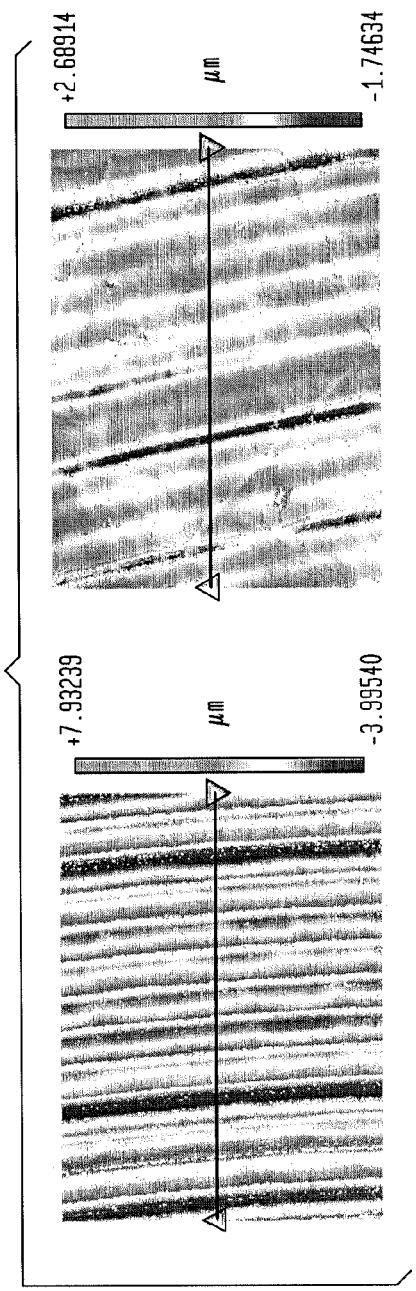
FIG. 2 shows a pair of comparative photographs of the photocrosslinked cup of FIG. 1 prior to wear testing on the left and after wear testing of 2.5 million cycles on the right as obtained using an interferometric profilometer.

FIG. 1 shows gravimetric wear (mg) of a cobalt chrome femoral head on a sequentially crosslinked (CoCr/X3®) cup and a similar cup with photocrosslinking and CoCr/X3®-PXL after 2.5 million cycles. No wear from CoCr/X3®-PXL was detected. The UHMWPE was initially crosslinked three times by the process described in U.S. Pat. No. 7,517,919. As shown in FIG. 2 it was also found that machine marks on the photocrosslinked cup were still visible after 2.5 million cycles.

Figure 3:
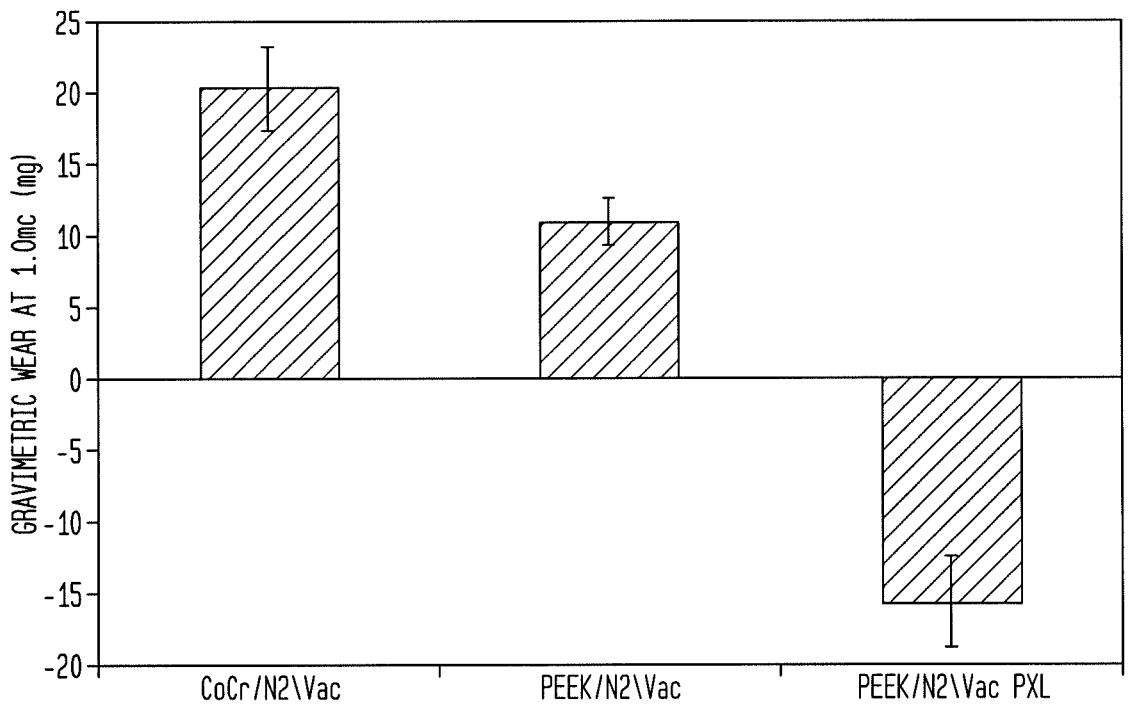
FIG. 3 shows the gravimetric wear of a PEEK surface on a photocrosslinked ultra high molecular weight polyethylene previously crosslinked in an inner atmosphere by gamma irradiation and a similar cup not photocrosslinked after one million cycles.

Similar results were observed in the wear testing of PEEK head on N2Vac treated cup and PEEK head on N2Vac plus PXL (FIG. 3). The cup was 28 mm in diameter with PEEK heads in a standard hip simulator. No wear was detected in PEEK/N2Vac-PXL after 1.0 million cycles while a non-photocrosslinked N2Vac cup produced more than 10 mg of gravimetric wear.

Figure 4:
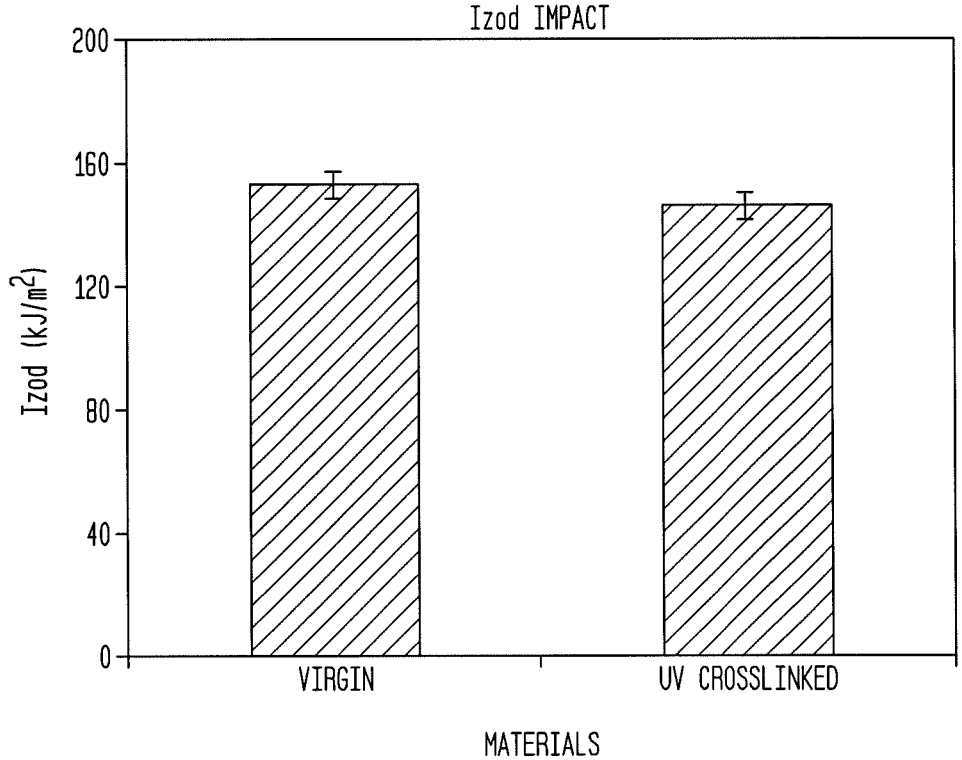
FIG. 4 shows an Izod impact energy before and after photocrosslinking of virgin ultra high molecular weight polyethylene showing no fracture toughness dropped after photocrosslinking with UV radiation.

FIG. 4 shows an Izod impact energy before and after photocrosslinking of virgin ultra high molecular weight polyethylene showing no fracture toughness dropped after photocrosslinking with UV radiation.

Figure 5:
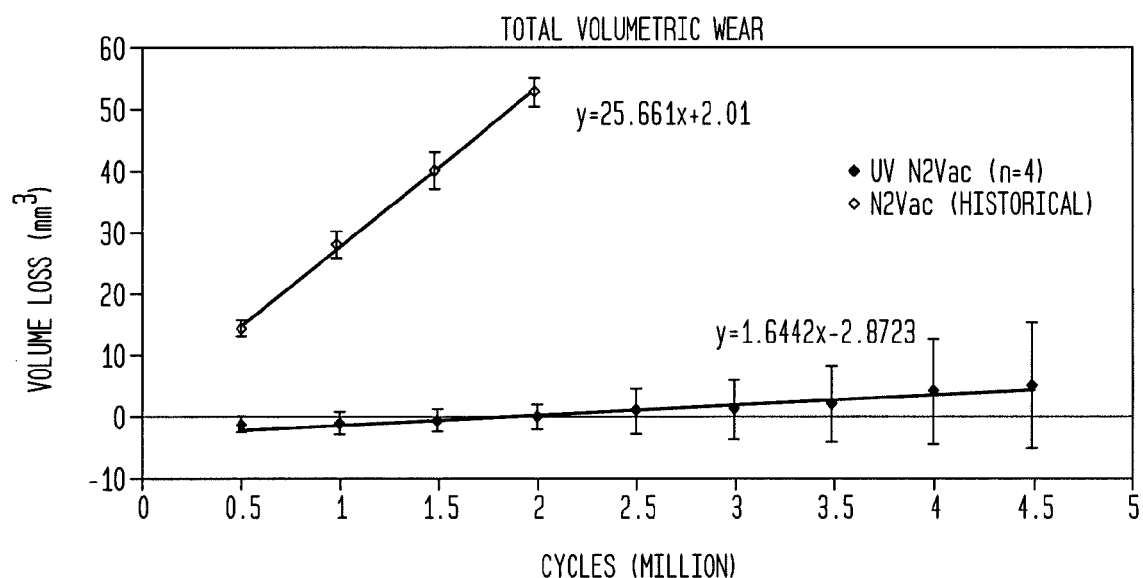
FIG. 5 is a graph showing the volumetric wear of a cobalt chrome prosthetic femoral head on an N$_2$VAC treated (3 Mrad gamma ray dose in an atmosphere of <1% oxygen and no subsequent annealing) UHMWPE bearing.

FIG. 5 is a graph showing the ASTM F-648-04 as tested by the volumetric wear of a cobalt chrome prosthetic femoral head on an $N_2VAC$ treated (3 Mrad gamma ray dose in an atmosphere of <1% oxygen and no subsequent annealing) UHMWPE bearing.

Figure 6:
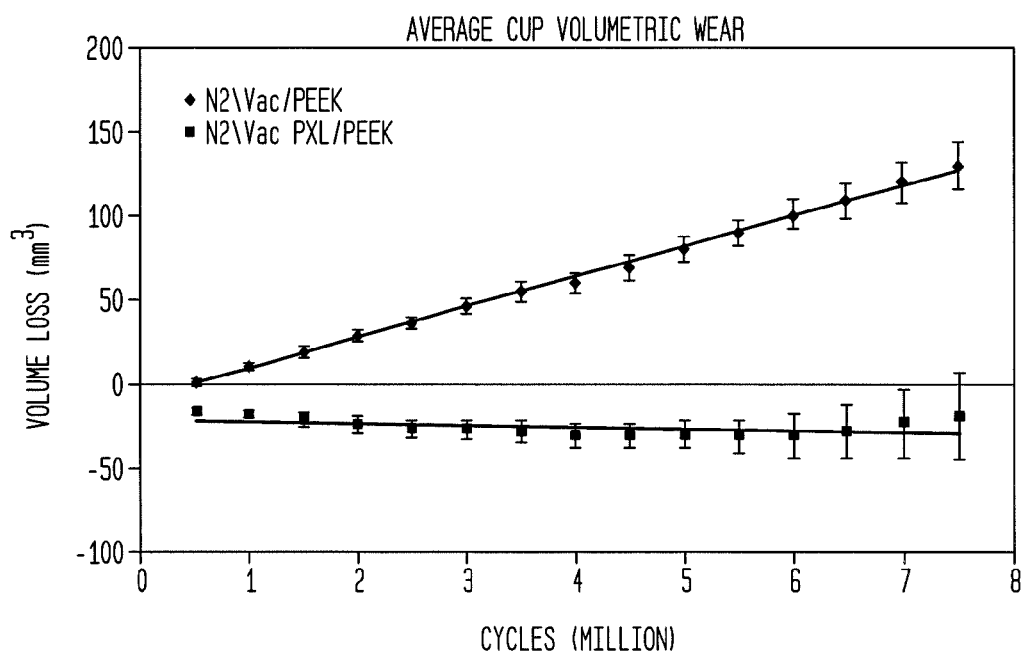
FIG. 6 is a graph showing the volumetric wear of a PEEK (polyether ether Ketone) prosthetic femoral head on an $N_2VAC$ treated UHMWPE bearing compared to the same bearing with UV photocrosslinking.

FIG. 6 is a graph showing the volumetric wear of a PEEK (polyether ether ketone) prosthetic femoral head on an $N_2VAC$ treated UHMWPE bearing.

Figure 7:
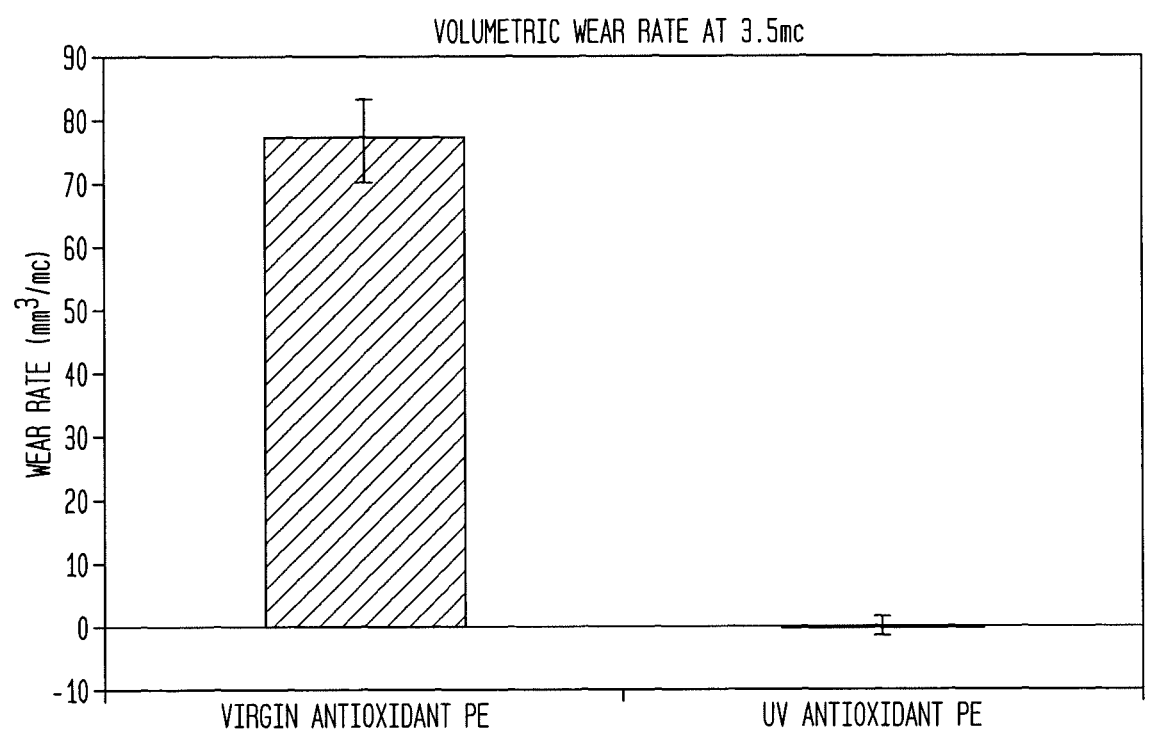
FIG. 7 is a graph showing the volumetric wear of Virgin Antioxidant doped UHMWPE compared to the same antioxidant treated UHMWPE with UV surface crosslinking at 3.5 million cycles (Mc).

FIG. 7 is a graph showing the volumetric wear of Virgin Antioxidant doped (with anthocyanin) UHMWPE compared to the same antioxidant treated UHMWPE with UV surface crosslinking both at 3.5 million cycles with the wear rate is in $mm^3$/million cycles.

An alternate method of coating the UHMWPE with benzophenone utilizes Physical Vapor Deposition process (PVD). The photoinitiator is evaporated into a gas by heating over its boiling temperature, then condensed onto UHMWPE bearing surface to form a uniform thin film. UV light is applied on the photoinitiator coated bearing surface and crosslinks the surface. Non-bearing surfaces may be masked to prevent being coated with a photoinitiator. Also a CVD method may be used to uniformly coat sensitizer (photoinitiator) on UHMWPE bearing surface. An alternative bearing combination could be UV crosslinked UHMWPE on UV crosslinked UHMWPE.

Any residual photoinitiator may advantageously be removed from preformed UHMWPE after photocrosslinking prior to fabrication of the implant. Alternately, if the implant is photocrosslinked after fabrication, the residual photoinitiator may be removed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for producing a wear resistant ultra-high molecular weight polyethylene medical implant comprising:
    forming a medical implant made at least partially of ultra-high molecular weight polyethylene (UHMWPE) with a bearing surface of the medical implant made of virgin UHMWPE;
    irradiating the medical implant with gamma ray or e-beam radiation to form free radicals and crosslinking the formed free radicals prior to exposure to air;
    thereafter coating the virgin UHMWPE bearing surface of the crosslinked medical implant with a uniform film of photoinitiator by evaporating the photoinitiator and then allowing it to condense onto the UHMWPE bearing surface;
    thereafter breaking carbon-hydrogen bonds in the UHMWPE by exposing the coated surface to ultra-violet (UV) radiation at an intensity of less than 100 $mW/cm^2$ and a wavelength between 300 and 400 nm; and
    thereafter removing the photoinitiator to produce a surface consisting essentially of crosslinked UHMWPE.

2. The method as set forth in claim 1 wherein the photoinitiator is Benzophenone.

3. The method as set forth in claim 1 wherein the medical implant is an orthopedic implant.

4. The method as set forth in claim 1 wherein the irradiation with gamma ray or e-beam radiation and crosslinking are performed in at least two sequential radiation doses.

5. The method as set forth in claim 4 wherein each radiation dose is less than 3.0 MRads.

6. The method as set forth in claim 1 wherein the UV and photoinitiator penetrate to a depth of less than about 1 mm.

7. The method as set forth in claim 1 wherein the implant is allowed to cool between gamma ray or e-beam crosslinking and the photocrosslinking.

8. A method for producing a wear resistant ultra-high molecular weight polyethylene (UHMWPE) medical implant consisting of:
- forming a medical implant comprising uniform UHMWPE, the medical implant including a bearing surface made of the uniform UHMWPE;
- irradiating the bearing surface with gamma ray or e-beam radiation to form free radicals and crosslinking the formed free radicals using heat prior to exposure to air;
- thereafter coating the uniform UHMWPE bearing surface of the crosslinked medical implant with a solution containing a photoinitiator selected from the group consisting of 2-methylanthraquinone, 2-ethylanthraquinone, 2-chloroanthraquinone, p-chloranil, benzyl sulfide, benzyl sulfoxide, phenyl sulfoxide, 4-acetylbiphenyl, anthrone, hexachlorobenzene, benzophenone, 4,4'-dimethoxybezophenone, 4-Nitrobenzophenone, 2-chlorobenzophenone, 4-chlorobenzophenone and 4,4'-dichlorobenzophenone;
- allowing the coating to dry;
- thereafter breaking carbon-hydrogen bonds in the UHMWPE surface by exposing the coated surface to ultraviolet (UV) radiation, thereafter removing the photoinitiator to produce a surface comprising crosslinked UHMWPE; and
- sterilizing the medical implant prior to implanting in the human body.

9. The method as set forth in claim 8 wherein the UV radiation has a wavelength of 300 to 400 mm.

10. The method as set forth in claim 9 wherein the intensity of the UV radiation is up to 100 mW/cm$^2$.

11. The method as set forth in claim 8 wherein the medical implant bearing surface is coated with the photoinitiator by immersion in the solution.

12. The method as set forth in claim 8 wherein the irradiation with gamma ray or e-beam radiation and crosslinking are performed in at least two sequential radiation doses.

13. The method as set forth in claim 12 wherein each radiation dose is less than 3.0 MRads.

14. The method as set forth in claim 8 wherein the UV and photoinitiator penetrate the bearing surface to a depth of less than about 1 mm.

15. The method as set forth in claim 8 wherein the implant is allowed to cool between crosslinking with heat and the photocrosslinking.

16. A method for producing a wear resistant ultra-high molecular weight polyethylene (UHMWPE) medical implant consisting essentially of:
- forming a medical implant comprising virgin UHMWPE;
- irradiating the medical implant UHMWPE with gamma ray or e-beam radiation to form free radicals and crosslinking the formed free radicals with heat;
- thereafter coating a bearing surface formed on the crosslinked medical implant with a photoinitiator;
- thereafter breaking carbon-hydrogen bonds by exposing the UHMWPE coated bearing surface to ultraviolet (UV) radiation and thereafter removing the photoinitiator to produce a surface comprising cross-linked UHMWPE; and
- sterilizing the medical implant prior to implanting in the human body.

17. The method as set forth in claim 16 wherein the bearing surface of the crosslinked medical implant is coated with the photoinitiator at a temperature of between 65° and room temperature.

18. The method as set forth in claim 16 wherein the photoinitiator is selected from the group consisting of 2-methylanthraquinone, 2-ethylanthraquinone, 2-chloroanthraquinone, p-chloranil, benzyl sulfide, benzyl sulfoxide, phenyl sulfoxide, 4-acetylbiphenyl, anthrone, hexachlorobenzene, benzophenone, 4,4'-dimethoxybezophenone, 4-Nitrobenzophenone, 2-chlorobenzophenone, 4-chlorobenzophenone and 4,4'-dichlorobenzophenone.

19. The method as set forth in claim 16 wherein the UV radiation has a wavelength of 300 to 400 mm.

20. The method as set forth in claim 19 wherein the intensity of the UV radiation is up to 100 mW/cm$^2$.

21. The method as set forth in claim 16 wherein the medical implant bearing surface is coated with the photoinitiator by vapor deposition or by immersion.

22. The method as set forth in claim 16 wherein the irradiation with gamma ray or e-beam radiation and crosslinking are performed in at least two sequential radiation doses.

23. The method as set forth in claim 22 wherein each radiation dose is less than 3.0 MRads.

24. The method as set forth in claim 16 wherein the UV and photoinitiator penetrate to a depth of less than about 1 mm.

25. The method as set forth in claim 16 wherein the implant is allowed to cool between crosslinking with heat and the photocrosslinking.

* * * * *